(12) United States Patent
Verruto et al.

(10) Patent No.: US 12,168,772 B2
(45) Date of Patent: Dec. 17, 2024

(54) METHOD OF TRANSFORMING PHOTOSYNTHETIC ORGANISMS

(71) Applicant: VIRIDOS, INC., La Jolla, CA (US)

(72) Inventors: John H. Verruto, San Diego, CA (US); Jessica N. Weir, San Diego, CA (US)

(73) Assignee: Viridos, Inc., La Jolla, CA (US)

( * ) Notice: Subject to any disclaimer, the term of this patent is extended or adjusted under 35 U.S.C. 154(b) by 517 days.

(21) Appl. No.: 17/307,824

(22) Filed: May 4, 2021

(65) Prior Publication Data
US 2021/0348183 A1  Nov. 11, 2021

Related U.S. Application Data

(60) Provisional application No. 63/020,414, filed on May 5, 2020.

(51) Int. Cl.
| | | |
|---|---|---|
| *C12N 15/82* | (2006.01) | |
| *C12N 1/12* | (2006.01) | |
| *C12N 9/10* | (2006.01) | |
| *C12Q 1/6806* | (2018.01) | |
| *C12R 1/89* | (2006.01) | |

(52) U.S. Cl.
CPC ......... *C12N 15/8269* (2013.01); *C12N 1/125* (2021.05); *C12N 9/1007* (2013.01); *C12Q 1/6806* (2013.01); *C12R 2001/89* (2021.05); *C12Y 201/01072* (2013.01)

(58) Field of Classification Search
None
See application file for complete search history.

(56) References Cited

U.S. PATENT DOCUMENTS

| | | | |
|---|---|---|---|
| 2007/0022485 A1 | 1/2007 | Takeda et al. | |
| 2010/0035945 A1* | 2/2010 | Cheng | A61P 31/04 |
| | | | 703/11 |
| 2011/0053273 A1* | 3/2011 | Benders | C12N 15/1024 |
| | | | 435/468 |
| 2016/0060643 A1* | 3/2016 | Wang | C12N 15/74 |
| | | | 435/471 |
| 2019/0024101 A1* | 1/2019 | Collin | C12N 15/8247 |
| 2022/0098599 A1* | 3/2022 | Johnston | C12N 15/74 |

OTHER PUBLICATIONS

Kim et al., "Improvement of Transformation Efficiency Through In Vitro Methylation and SacII Site Mutation of Plasmid Vector in Bifidobacterium longum MG1", Journal of Microbiology and Biotechnology, Apr. 2010, 20(6):1022-1026.

PCT International Search Report and Written Opinion in International Application No. PCT/US2021/030693, dated Sep. 17, 2021, 8 pages.

Wang et al., "Premethylation of Foreign DNA Improves Integrative Transformation Efficiency in *Synechocystis* sp. Strain PCC 6803", Applied and Environmental Microbiology, Oct. 2015, 81(24):8500-8506.

* cited by examiner

*Primary Examiner* — Christian L Fronda
(74) *Attorney, Agent, or Firm* — Viridos, Inc.

(57) ABSTRACT

The invention provides methods of transforming photosynthetic organisms, such as green algae. The methods involve methylating one or more DNA fragments of a DNA construct and transforming the one or more fragments into the photosynthetic organism. The DNA fragments can be the product of a DNA amplification procedure, such as PCR or a PCR-like procedure. In one embodiment the one or more fragments of DNA that comprise a DNA construct are dam methylated prior to being transformed into the photosynthetic organism.

14 Claims, 4 Drawing Sheets

Figure 1:
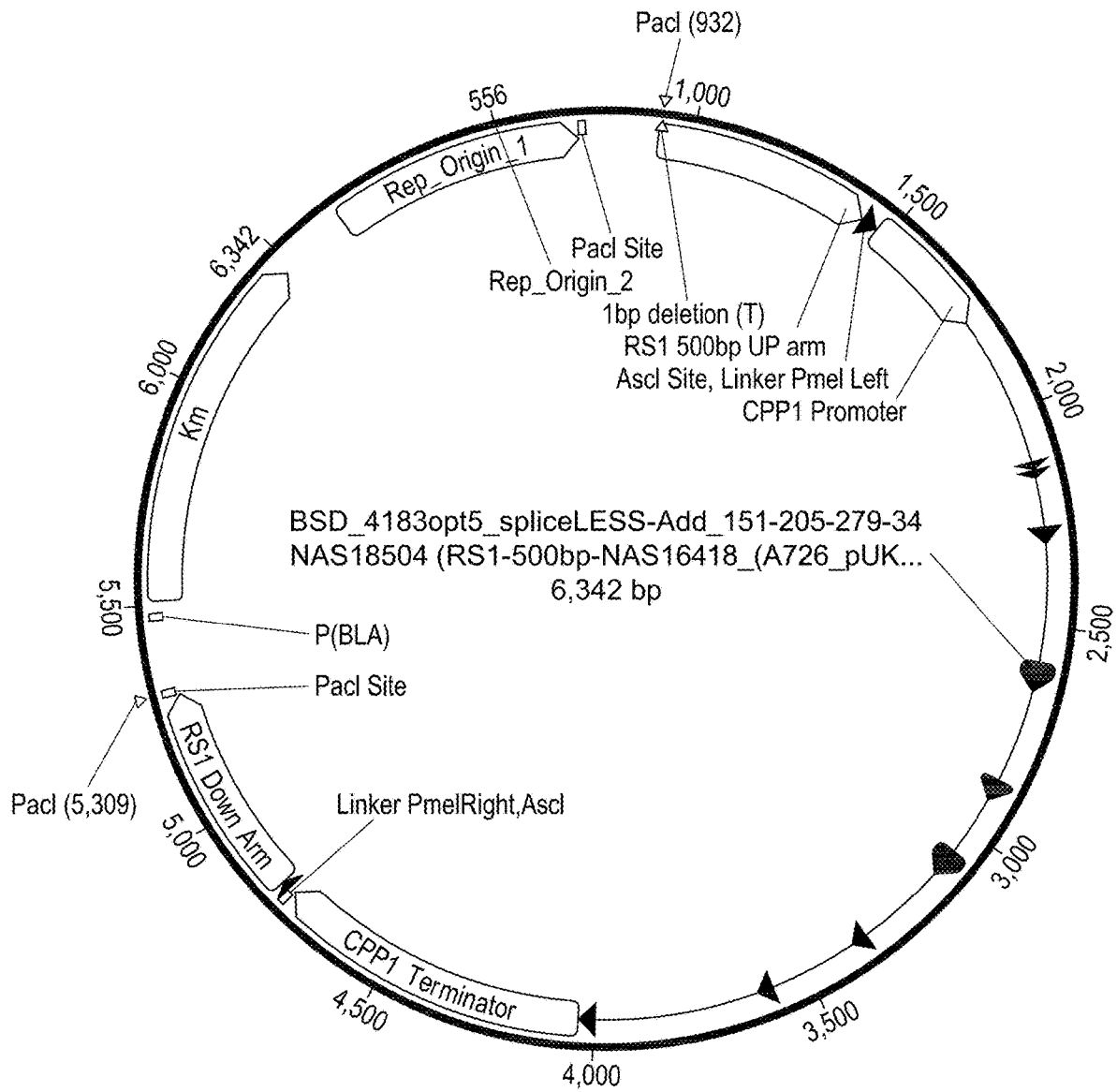

| Key | Enzyme | Recognition sequence | Cuts | Blocked |
|---|---|---|---|---|
| 1 | | | uncut | |
| 2 | DpnI | GATC | Dam Methylated (10 sites) | Overlapping CpG |
| 3 | DpnII | GATC | 10 sites | dam methylation |
| 4 | HpaII | CCGG | 9 sites | CpG methylation |
| 5 | MspI | CCGG | 9 sites | None |

METHOD OF TRANSFORMING PHOTOSYNTHETIC ORGANISMS

CROSS-REFERENCE TO RELATED APPLICATIONS

This application claims benefit of priority under 35 U.S.C. § 119(e) of U.S. Ser. No. 63/020,414, filed May 5, 2020, the entire contents of which is incorporated herein by reference in its entirety.

FIELD OF THE INVENTION

The invention involves the transformation of photosynthetic organisms with DNA molecules.

BACKGROUND OF THE INVENTION

Eukaryotic algae are a diverse group of organisms of great ecological and commercial importance. Transformation of these organisms is complicated by the presence of a cell wall and has been accompanied by problems with efficiency, integration, or stability of transgenes. As a result, genetic transformation of algal species has lagged behind that of other organisms. Nevertheless, some techniques do exist for certain algae, but a lack of knowledge about the requirements for transforming algae has resulted in poor efficiency and other disadvantages. For transformations into many algae PCR products have been found to provide very poor rates of transformation and colony formation.

There is therefore a continuing need for development of techniques and methods for the successful transformation of algae and resultant high colony formation rates so that the potential of these organisms can be more fully utilized in biological studies.

SUMMARY OF THE INVENTION

The invention provides methods of transforming photosynthetic organisms, such as green algae. The methods involve contacting one or more DNA fragments that comprise a DNA construct with a methylating enzyme to thereby methylate the one or more DNA fragments, and transforming the one or more DNA fragments into the photosynthetic organism. The DNA fragments that comprise the construct can be the product of a DNA amplification procedure (e.g. PCR or a variant of PCR). In one embodiment the one or more fragments of DNA that comprise a DNA construct are dam methylated prior to being transformed into the photosynthetic organism.

In a first aspect the invention provides methods of transforming a photosynthetic organism. The methods involve contacting at least one DNA fragment with a DNA methylating enzyme to produce at least one methylated DNA fragment; and transforming the photosynthetic organism with the at least one methylated DNA fragment. In any embodiment the contacting can be done in vitro. In some embodiments the DNA methylating enzyme can be a methyltranferase. In some embodiments the DNA methylating enzyme can perform m6A methylation. In some embodiments the DNA methylating enzyme can be a prokaryotic DNA methylating enzyme. In various embodiments the methylating enzyme can be a methyltransferase performs dam methylation.

In some embodiments the at least one DNA fragment is a plurality of DNA fragments that together comprise a DNA construct. The at least one DNA fragment can be assembled into the DNA construct prior to transforming the photosynthetic organism, or can be transformed as DNA fragments and assembled in the host cell or organism. The at least one DNA fragment can be the product of digestion with a restriction endonuclease. In one embodiment the transforming can be performed using a biolistic method. In any embodiment the photosynthetic organism can be a Chlorophyte alga. The Chlorophyte alga can be an alga of the Class Trebouxiophyceae. And in one embodiment the alga of the Class Trebouxiophyceae alga is of the family Oocystacea. In one embodiment the alga is of the genus *Oocystis*.

In some embodiments transforming the at least one methylated DNA fragment is performed by particle bombardment. The transformation construct can be a plasmid having any one or more of a promoter, a gene of interest, and a terminator. The transformation construct can also have an origin of replication and/or a selectable marker. The transformation construct can also have all of a promoter, a gene of interest, a terminator, an origin of replication, and a selectable marker, or any possible combination or subcombination of them.

In some embodiments the at least one DNA fragment is provided as a linear fragment. The at least one DNA fragment can be dam methylated. In various embodiments the at least one DNA fragment is not CpG methylated. In some embodiments the methylase can be a deoxyadenosine (Dam) methylase.

DETAILED DESCRIPTION OF THE DRAWINGS

FIG. 1 provides an illustration of an uncut pUK-derived vector containing the integration fragment.

Figure 2:
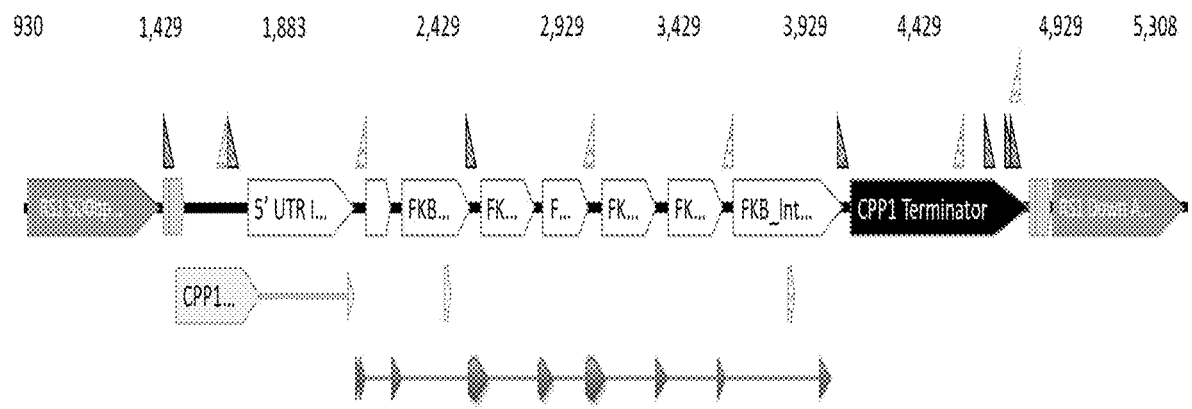

FIG. 2 provides a schematic illustration of a linearized fragment of the plasmid from FIG. 1 that was transformed into *Oocystis* sp. and showing possible methylation sites.

Figure 3:
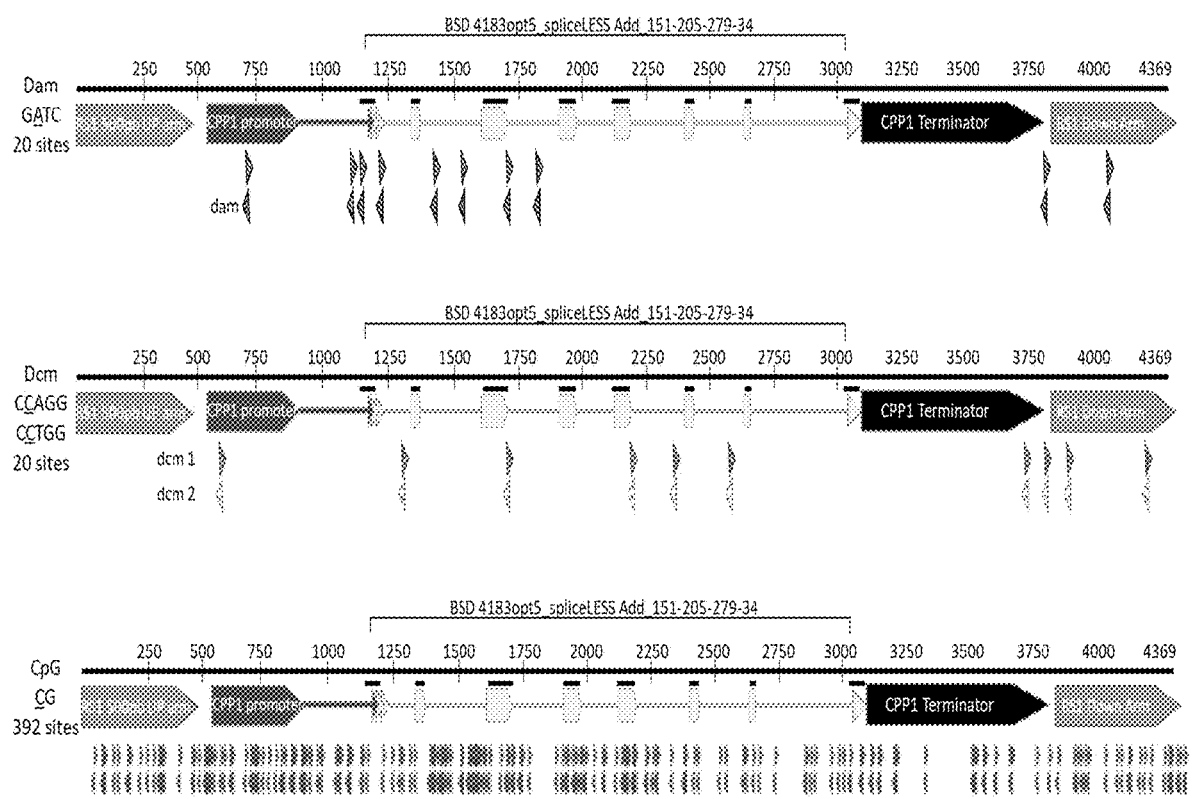

FIG. 3 provides a schematic illustration of possible methylation sites for dam, dcm, and CpG methyltransferases on the integration fragment transformed into *Oocystis* sp. dcm1 (CCAGG), dcm2 (CCTGG), and CpG (CG) sites are indicated.

Figure 4:
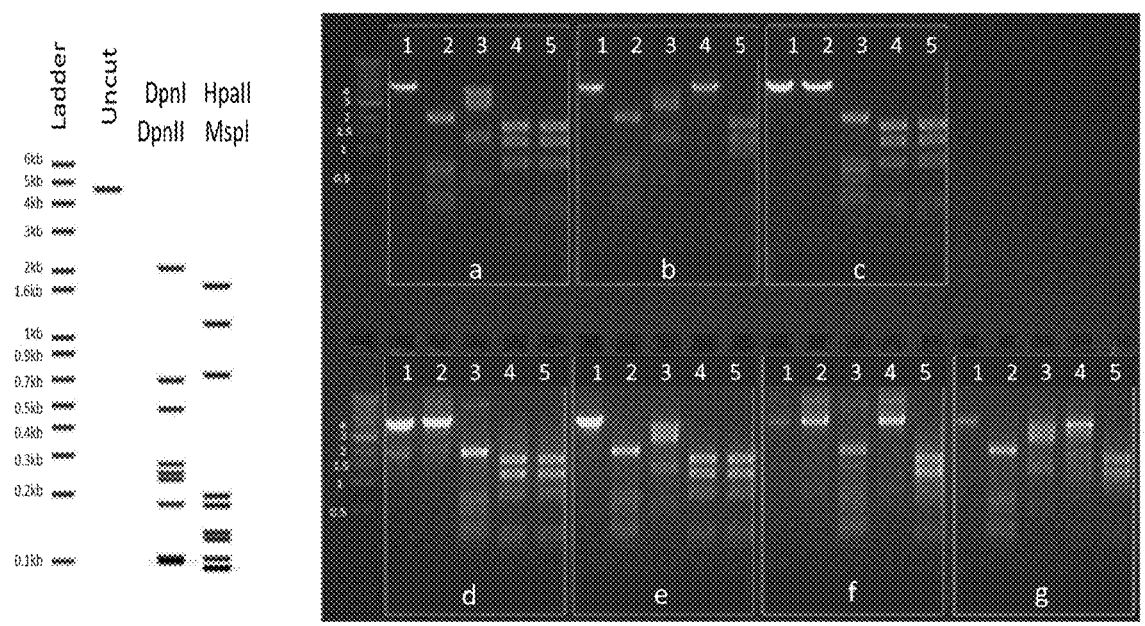

FIG. 4 is an illustration of restriction digests confirming complete methylation of DNA fragments. In the Figure the top three gels are plasmid constructs that are a) PacI digested gel-purified, b) PacI digested, gel-purified, CpG+, and c) PacI digested gel-purified, dam negative-dcm negative. The bottom four gels are PCR amplified constructs: d) PCR-amplified fragments, e) PCR amplified, dam+, f) PCR amplified CpG+, and g) PCR-amplified CpG+, dam+. In all gels the lanes are 1. Uncut, 2. DpnI, 3. DpnII, 4. HpaII, and 5. MspI, in that order.

DETAILED DESCRIPTION OF THE INVENTION

The invention discloses methods of transforming photosynthetic organisms. The methods involve the methylation of DNA constructs or parts of DNA constructs, which in some embodiments can be done in vitro, before transformation into photosynthetic microorganisms. The invention provides high rates of successful transformation and colony formation.

The present inventors discovered unexpectedly that when a DNA construct (or the parts or fragments of a DNA construct) is subjected to methylation prior to being transformed into photosynthetic microorganisms, much higher rates of transformation and colony formation (containing the construct) were observed. This discovery enables the use of PCR products in the transformation of photosynthetic and green algae. The invention therefore allows for the fast generation of specifically tailored DNA by PCR and its subsequent transformation into photosynthetic microorganisms with high transformation and colony formation rates. The need for time-consuming cloning processes to generate DNA constructs for each target of homologous recombination can therefore be eliminated.

DNA Methylation

DNA methylation is a process by which methyl groups are added to a DNA molecule. Such methylation can change the activity of DNA. For example, DNA methylation in bacteria is important in gene expression and DNA replication. DNA methylation has been believed to be important in prokaryotic organisms. When occurring in eukaryotes, DNA methylation has been believed to occur primarily or exclusively at the cytosine residue of CpG sequences, leading to the formation of 5-methylcytosine. In plant genomes DNA methylation can occur symmetrically at cytosines in both CG and CHG (H=A, T, or C) contexts. In *Arabidopsis thaliana* for example, levels of cytosine methylation at CG, CHG, and CHH nucleotides are about 24%, 6.7%, and 1.7%, respectively.

Prokaryotes (e.g. *E. coli*) have three site-specific DNA methylating enzymes, any of which can find use in the methods of the invention: 1) Dam methylases (deoxyadenosine methylase), which methylate the N6 position of adenine in GATC sequences; 2) Dcm methyltransferases (DNA cytosine methyltransferase), which methylate the C5 position of the second cytosine in CCAGG and CCTGG sequences; and 3) a EcoKI methylase, which methylates adenine in the sequences AAC(N6)GTGC and GCAC(N6)GTT. DNA methyltransferases (MTases) can transfer a methyl group from S-adenosylmethionine to either adenine or cytosine residues. In eukaryotes, CpG methyltransferases (e.g. Dnmt1) transfer a methyl group to the C5 position of cytosine residues (CG). In each case the underlined nucleotide is methylated by the enzyme. Methylating enzymes include methylases and methyltransferases, both of which can find use in the invention. There are many methylating enzymes and those disclosed here are provided only as examples. Thus, in one embodiment of the methods the methylating enzyme methylates the N6 position of adenine in GATC sequences; the methylating enzyme can be encoded by the dam gene. A methylating enzyme that methylates 6-adenine (e.g. in the sequence GATC) is described herein as an m6A methylase (i.e. performs m6A methylation). In one embodiment of the methods the methylating enzyme is an m6A methylase. In any embodiment the at least one DNA fragment can be methylated by contact with a dam methylase. In any embodiment the at least one DNA fragment can be dam methylated. There are also non-specific methylating enzymes, for example EcoGII methyltransferase, which modifies adenine (N6) in any sequence context. In any embodiment the DNA methylating enzyme can be a prokaryotic DNA methylating enzyme, such as any described herein. A prokaryotic DNA methylating enzyme is one naturally found in prokaryotic organisms. In any embodiment the DNA methylating enzyme can be a heterologous DNA methylating enzyme. In any embodiment the at least one DNA fragment can lack CpG methylation. Any of the methylating enzymes disclosed herein can be utilized in the invention. In any embodiment of the methods the at least one DNA fragment contacted with the DNA methylating enzyme is a product of PCR or a PCR variant, non-limiting examples of which include multiplex PCR, asymmetric PCR, nested PCR, quantitative PCR, hot-start PCR, touchdown PCR, assembly PCR, colony PCR, the digital polymerase reaction, suicide PCR, COLD-PCR, or another amplification procedure. In any embodiment the DNA fragment can be unmethylated, or not have been subjected to a methylation procedure. In one embodiment the DNA fragment contacted with the DNA methylating enzyme is an unmethylated fragment.

The invention provides methods of transforming photosynthetic organisms. The photosynthetic microorganism can be a microalga or a green alga. In any embodiment the photosynthetic organism can be a recombinant microorganism. The photosynthetic microorganism can be any eukaryotic alga or microalga such as, but not limited to, a Chlorophyte, an Ochrophyte, or a Charophyte alga. In some embodiments the microorganism can be a Chlorophyte alga of the taxonomic Class Chlorophyceace, or of the Class Chlorodendrophyceae, or the Class Prasinophyceace, or the Class Trebouxiophyceae, or the Class Eustigmatophyceae. In some embodiments, the microorganism can be a member of the Class Chlorophyceace, such as a species of any one or more of the genera *Asteromonas, Ankistrodesmus, Carteria, Chlamydomonas, Chlorococcum, Chlorogonium, Chlorodendrales, Chloroellales, Chrysosphaera, Dunaliella, Haematococcus, Monoraphidium, Neochloris, Oedogonium, Pelagomonas, Pleurococcus, Pyrobotrys, Scenedesmus*, or *Volvox*. In other embodiments, the microalga can be a member of the Class Chlorodendrophyceae, such as a species of any one or more of the genera *Prasinocladus, Scherffelia*, or *Tetraselmis*. In further alternative embodiments, the alga can be a member of the Class Prasinophyceace, optionally a species of any one or more of the genera *Ostreococcus* or *Micromonas*. Further alternatively, the microalga can be a member of the Class Trebouxiophyceae, and optionally of the Order Chlorellales, and optionally a genera selected from any one or more of *Botryococcus, Chlorella, Auxenochlorella, Heveochlorella, Marinichlorella, Oocystis, Parachlorella, Pseudochlorella, Tetrachlorella, Eremosphaera, Franceia, Micractinium, Nannochloris, Picochlorum, Prototheca, Stichococcus*, or *Viridiella*, or any of all possible combinations or sub-combination of the genera. In another embodiment the alga is a Chlorophyte alga of any of Class Trebouxiophyceae, the Order Chlorellales, the Family Oocystaceae, Chlorellaceae, or Eustigmatophyceae, and optionally a genera selected from one or more of *Oocystis, Parachlorella, Picochlorum, Nannochloropsis*, and *Tetraselmis* in all possible combinations or sub-combinations. The alga can also be from the genus *Oocystis*, or the genus *Parachlorella*, or the genus *Picochlorum*, or the genus *Tetraselmis*, or from any of all possible combinations and sub-combinations of these genera.

DNA Constructs

DNA constructs are molecules of DNA constructed using molecular biology techniques that can be transformed into a targeted microorganism. In one embodiment the DNA construct is a plasmid. In any embodiment a DNA construct can be provided as one or more DNA fragments. The plasmid can be useful for transforming algal cells. In various embodiments DNA constructs can have one or more of a promoter sequence, a gene of interest (GOI), and a transcription terminator or polyadenylation signal sequence (poly-A), or all of these structures. DNA constructs can also, optionally, have a selectable marker (e.g. one or more antibiotic resistance genes) and/or an origin of replication. The DNA construct can comprise a single DNA fragment or can be comprised of a plurality of DNA fragments. Each DNA fragment in a plurality of DNA fragments can comprise a portion of a DNA construct. In the methods the plurality of DNA fragments can be assembled prior to transformation into a cell or microorganism. The assembly of DNA constructs from a plurality of DNA fragments is required in many applications of molecular biology, and many such techniques are known. The DNA construct can also be assembled from the fragments by the cell or microorganism. In various embodiments the DNA construct can be assembled from 4 or more, or 6 or more, or 8 or more fragments or 10 or less, or 20 or less or 25 or less or 30 or less or 2-10 or 2-20 or 2-30 or more than 30 fragments of DNA. A transformation construct is a vehicle for carrying genetic material into a cell. The genetic material can be heterologous DNA. Heterologous DNA is a sequence of DNA from a species or origin other than the cell or organism the DNA is introduced into. Heterologous sequences can also be synthetic and not derived from the cell or organism. In any embodiment a transformation construct can be a linear fragment or a circular DNA. In any embodiment the DNA construct can be transformed into the cell or microorganism as one or more linear DNA fragments or as circular DNA.

In one embodiment the DNA fragments that are transformed into the photosynthetic organism of the invention are methylated. The methylation can be done enzymatically and in vitro, or by any method described herein. In one embodiment the DNA fragments are products of a DNA amplification procedure, for example PCR or a variant of PCR. The fragments can be methylated as disclosed herein after performing a DNA amplification procedure. In another embodiment the DNA fragments transformed into the photosynthetic organism of the invention can be the products of cloning in an organism that does not methylate DNA. In any embodiment the DNA fragments transformed into the photosynthetic organism of the invention can be the products of cloning in an organism that does not dam methylate DNA. In any embodiment the DNA fragments transformed into the photosynthetic organism of the invention can be the products of cloning in an organism that does not have a dam methylase. In any embodiment the DNA fragments can be the product of digestion with one or more restriction endonuclease(s). In any embodiment the DNA fragments can be methylated by an enzyme that is not endogenous to the organism the DNA is transformed into in a later step, or that is not endogenous to an organism the DNA was amplified in.

Preparation and Transformation

Transformation refers to the process of introducing exogenous DNA into cells, which can be plant or algal cells. Transformation of a cell or microorganism of the invention can occur by any convenient means. In various embodiments electroporation or particle bombardment methods can be used to accomplish transformation. In any embodiment the cells transformed in the method can be competent cells. In some embodiments the DNA fragments comprising the DNA construct can be methylated prior to transformation. Persons of ordinary skill with resort to this disclosure will realize that cells can be made competent according to various methods, for example by electroporation or heat shock of chemically prepared competent cells; for example cells can be grown up in culture and harvested in mid-log phase. If electroporation is to be used harvested cells can be washed with cold water or sorbitol by repeatedly pelleting and resuspension to remove salts and other components that could interfere with transformation, with final pelleting and resuspension in glycerol. When cells are to be transformed by heat shock they can be incubated in calcium chloride, which can be supplemented with other ions (e.g. manganese, potassium, cobalt, rubidium, dimethylsulfoxide and dithiothreitol). Other methods of preparing competent cells can also be used.

Methods of transformation can include any suitable method. In various embodiments transformation can be accomplished by biolistic methods, electroporation, or heat shock of chemically prepared competent cells. Electroporation can involve the use of a commercially available electroporator to expose cells to a brief pulse of a high-voltage electric field resulting in a temporary rearrangement of the cell membrane and membrane permeability. In some embodiments the electric pulse can utilize exponential decay (or capacitance discharge), where a set voltage is applied and allowed to decay over a few milliseconds.

In other embodiments the heat shock method can be used to transform the cells. In one embodiment heat shock can be performed at 37-42° C. for 25-45 seconds, but persons of ordinary skill in the art with resort to the present disclosure will realize other effective protocols.

Methylation can be performed by contacting at least one DNA fragment described herein with a DNA methylating enzyme described herein to produce at least one methylated DNA fragment. The methylation can be performed using any method described herein. The contacting can be done in vitro. The at least one methylated DNA fragment is thereby transformed into the cell or organism of the invention.

EXAMPLES

A pUC19-based vector was constructed containing a selectable marker cassette encoding a blasticidin resistance gene flanked by 500 bp of *Oocystis* genomic sequence on either side and controlled by endogenous promoters and terminators, all within restriction sites for PacI restriction enzyme. This vector was initially constructed in *E. coli* DH5a cells, which perform both dam and dcm methylation (Me positive). The base vector was also purified using a commercially available "miniprep" kit and transformed into competent *E. coli* cells negative for both dam and dcm methylation enzymes (dam-, dcm-) using standard methods (Me negative) provided by the manufacturer.

To prepare DNA for methylation treatment the plasmids from both the Me-positive and Me-negative cell lines were purified using a commercially available "miniprep" kit and either PacI digested or PCR amplified to create linear fragments (FIG. 2) using standard methods. The fragments from the DH5a cells (which were methylated by the organism) were then amplified via PCR, thus resulting in unmethylated product fragments. Methylation treatments were then performed on these PCR product fragments. FIG. 2 shows that the integration fragment contained sufficient possible methylation sites to distinguish between treatments that went to completion and those that did not. And FIG. 3 shows 20 possible dam methylation sites (GATC), 20 possible dcm methylation sites (CCAGG), and 392 possible CpG methylation sites on the fragment.

Methylation treatments were done using enzymes sourced from commercial sources and according to manufacturer suggested protocols. Dam methylation was performed with dam methyltransferase sourced from *E. coli* carrying the plasmid pTP166, which had the dam modification gene. CpG methylation was performed by the CpG methyltransferase (M.SssI). Methylation was tested for completion by restriction digestion with DpnI, DpnII, HpaII and MspI. DpnI and DpnII have the same recognition sequence (GATC) but DpnI only cuts dam-methylated DNA (G$\underline{A}$TC) and is blocked by overlapping CpG methylation, while DpnII is blocked by dam methylation. HpaII and MspI have the same recognition sequence (CCGG) but HpaII is blocked by CpG methylation and MspI is not blocked by any methylation. M.SssI is a CpG methyltransferase.

FIG. 4 shows seven gels, which are
a) PacI digested gel-purified,
b) PacI digested, gel-purified, CpG+ (positive),
c) PacI digested gel-purified, dam negative, dcm negative,
d) PCR-amplified fragments,
e) PCR amplified, dam+ (positive),
f) PCR amplified CpG+ (positive), and
g) PCR-amplified CpG+ (positive), dam+ (positive).

The data summarized in FIG. 4 show that the DnpII digest of plasmid alone showed some cutting, indicating it can be further dam-methylated. The HpaII digest was completely blocked by CpG methylation of the plasmid and PCR products (top row, middle; bottom row, third gel), but partly able to cut PCR fragments treated with Dam and CpG methyltransferases. The DpnI digest of all dam-methylated DNA went to completion in each treatment, both plasmid and PCR products. The MspI digest, which is not blocked by any methylation, showed cutting in all gels.

After the methylation treatments the DNA fragments were transformed into *Oocystis* sp. using a gene gun. DNA was precipitated onto gold particles, which were adhered to the inside of tubing, and helium gas was fired through the tubing to project the DNA-coated gold particles into cells adhered on solid non-selective media. The following day the cells were moved onto selective media for growth and screening of transformed colonies. Colonies were counted after seven days to compare the effects of DNA methylation on transformation efficiency.

TABLE 1

Colony counts from transformation into *Oocystis* sp.

| DNA Source | Treatment 1 | Treatment 2 | Treatment 3 | Methylation | Colonies |
|---|---|---|---|---|---|
| DH5a plasmid | Restriction digest, gel purification | N/A | N/A | dam, dcm | 114 |
| DH5a plasmid | Restriction digest, gel purification | M. SssI treatment, spin purification | N/A | dam, dcm, CpG | 13 |
| dam⁻dcm⁻ plasmid* | Restriction digest, gel purification | N/A | N/A | None | 1 |
| DH5a plasmid | PCR amplification, gel purification | N/A | N/A | None | 0 |
| DH5a plasmid | PCR amplification, gel purification | Dam methylation, spin purification | N/A | dam | 153 |
| DH5a plasmid | PCR amplification, gel purification | M. SssI treatment, spin purification | N/A | CpG | 1 |
| DH5a plasmid | PCR amplification, gel purification | M. SssI treatment, spin purification | Dam methylation, spin purification | dam, CpG | 124 |

*dam negative and dcm negative.

The data show that dam methylation provided much higher levels of colony formation than unmethylated DNA, yielding over 100 colonies. In contrast, only one colony was produced by the dam negative/dcm negative unmethylated DNA. CpG-methylated DNA provided lower colony counts in spite of the *Oocystis* genome being highly CpG methylated.

The experiment was expanded to include treatments with additional methylating enzymes that have different methylation patterns. The additional methylating enzymes used were EcoGII, AluI, HaeIII, and MspI. EcoGII adds m6A methylation (providing N6-methyl adenosine) to adenines without sequence specificity; AluI and HaeIII add non-CpG methylation (to 22 and 30 possible sites, respectively), and MspI was also used, which performs CHG methylation.

TABLE 2

Colony counts from transformation into Oocystis (with DNA fragments subjected to additional methylation)

| DNA Source | Treatment 1 | Treatment 2 | Methylation | Colonies |
|---|---|---|---|---|
| DH5a plasmid | Restriction digest, gel purified | N/A | Dam, Dcm | 104 |
| DH5a plasmid | Restriction digest, gel purified | Dam methylation, spin purification | Dam, Dcm | 104 |
| DH5a plasmid | PCR amplification, spin purified | N/A | N/A | 2 |
| DH5a plasmid | PCR amplification, spin purified | Dam methylation, spin purification | Dam | 122 |
| DH5a plasmid | PCR amplification, spin purified | M. SssI treatment, spin purification | CpG | 0 |
| DH5a plasmid | PCR amplification, spin purified | EcoGII treatment, spin purification | Nonspecific m6A | 58 |
| DH5a plasmid | PCR amplification, spin purified | AluI treatment, spin purification | Non-CpG methylated DNA (some CHG) | 1 |
| DH5a plasmid | PCR amplification, spin purified | MspI treatment, spin purification | CHG | 0 |
| DH5a plasmid | PCR amplification, spin purified | HaeIII treatment, spin purification | Non-CpG methylated DNA (some CHG) | 1 |

The data show that dam methylation alone provided a much higher rate of colony formation than non-methylated DNA and substantially higher than other types of methylation.

In a further step a dam negative/dcm negative (dam⁻, dcm⁻) plasmid was subjected to either a step of dam methylation or to no treatment before being re-transformed into *Oocystis* sp.

TABLE 3

| DNA Source | Treatment 1 | Treatment 2 | Treatment 3 | Methylation | Colonies |
|---|---|---|---|---|---|
| dam– dcm– plasmid | Restriction digest, gel purification | N/A | N/A | None | 0 |
| dam– dcm– plasmid | Restriction digest, gel purification | Dam methylation, spin purification | N/A | Dam | 64 |

The data show substantial colony formation for the dam-methylated plasmid and no colonies for the dam/dcm negative plasmid. Re-transformation of the same unmethylated plasmid produced no colonies.

What is claimed is:

1. A method of transforming a photosynthetic Trebouxiophyte organism comprising:
contacting at least one DNA fragment with a dam methyltransferase to produce at least one methylated DNA fragment; and
transforming the photosynthetic Trebouxiophyte organism with the at least one methylated DNA fragment.

2. The method of claim 1 wherein the contacting is done in vitro.

3. The method of claim 2 wherein the DNA methylating enzyme performs m6A methylation.

4. The method of claim 2 wherein the dam methyltransferase is a prokaryotic dam methyltransferase.

5. The method of claim 2 wherein the at least one DNA fragment comprises a plurality of DNA fragments and together the plurality of DNA fragments comprise a DNA construct.

6. The method of claim 5 wherein the plurality of DNA fragments are assembled into the DNA construct prior to transforming the photosynthetic Trebouxiophyte organism.

7. The method of claim 5 wherein the at least one DNA fragment is a product of digestion with a restriction endonuclease.

8. The method of claim 2 wherein the organism is transformed using a biolistic method.

9. The method of claim 1 wherein the Trebouxiophyte alga is of the family Oocystacea.

10. The method of claim 5 wherein the DNA construct is a plasmid comprising a promoter, a gene of interest, and a terminator.

11. The method of claim 10 wherein the plasmid further comprises an origin of replication and/or a selectable marker.

12. The method of claim 9 wherein the alga is of the genus *Oocystis*.

13. The method of claim 2 wherein the at least one DNA fragment is provided as one or more linear fragment(s).

14. The method of claim 2 wherein the at least one DNA fragment is dam methylated.

* * * * *